United States Patent [19]
Miljkovic et al.

[11] Patent Number: 6,080,425
[45] Date of Patent: *Jun. 27, 2000

[54] BORON COMPOUNDS AND COMPLEXES AS SKIN-REJUVENATING AGENTS

[75] Inventors: Dusan Miljkovic, San Diego; Zbigniew Pietrzkowski, Foothill Ranch, both of Calif.

[73] Assignee: TopGene, Inc., Fullerton, Calif.

[*] Notice: This patent is subject to a terminal disclaimer.

[21] Appl. No.: 09/192,814

[22] Filed: Nov. 16, 1998

Related U.S. Application Data

[60] Provisional application No. 60/086,826, May 26, 1998.

[51] Int. Cl.[7] ............................ A61K 9/127; A61K 7/00; A61K 9/107
[52] U.S. Cl. .......................... 424/450; 424/401; 424/657; 514/23; 514/844; 514/881; 514/937
[58] Field of Search ..................... 424/450, 401, 424/657; 514/23, 844, 881, 937

[56] References Cited

U.S. PATENT DOCUMENTS

5,628,990   5/1997   Murphy ........................ 424/65

*Primary Examiner*—Gollamudi S. Kishore
*Attorney, Agent, or Firm*—Robert D. Fish; Fish & Associates, LLP

[57] ABSTRACT

Boron compounds/complexes, other than boric acid and boric acid salts, are utilized for rejuvenating of skin. The compounds/complexes have a central tetrahedral boron atom covalently bound to four ligands, which may be either identical or different from each other. Preferred ligands include an oxygen, nitrogen, carbon or sulfur atom, and more preferred ligands are saccharides or amino acids that form stable five- or six-membered rings with the boron atom. Especially preferred compounds have a dissociation constant of at least 3,000, and include a saccharide. Especially preferred complexes include a sodium, potassium, magnesium or calcium cation. The compounds/complexes are useful in rejuvenating skin, including decreasing skin wrinkles, improving skin thickness, increasing skin hydration, softness and elasticity, improving the skin color, and decreasing the number and size of age spots. The compounds/complexes are preferably provided in a suitable solvent system, a microemuslion or macroemulsion form, or a suitable liposome, and may be applied in any suitable form, including creams, bath salts, cosmetics, and shampoos.

12 Claims, 7 Drawing Sheets

BORON COMPOUNDS AND COMPLEXES AS SKIN-REJUVENATING AGENTS

This application is a continuation of Provisional application No. 60/086,826 filed May 26, 1998.

FIELD OF THE INVENTION

The field of the invention is skin rejuvenating agents, especially agents that increase collagen production.

BACKGROUND OF THE INVENTION

Biological Activity and Use of Boron Compounds

Boron compounds are known to show a variety of different biological activities. Very often, boron compounds snow enzyme inhibitory activity, including inhibition of a number of enzymes. These functions have been demonstrated alone, and in combination with various co-inhibitors. For example, borates have been demonstrated to inhibit L-amino acid oxidase in a mixture with butanediol, by interacting with the arginine residue in the active site. (Christman M F, Cardenas J M: Experientia 38(5): 537–538 (1982)).

Borates and butanediol are also known to inhibit citrate/isocitrate-hydro-lyase, EC 4.2.1.3, again by interacting with the arginine residue from the active site. (Gawron O, Jones L: Biochem Biophys Acta 484 (2): 453–464 (1977)). Also, 2,3-butanediol or 1,2-cyclohexanedione in the presence of borates interacts specifically with the guanidino group from arginine, and this fact was used for determination of arginine residues in the active site of the examined enzymes. In this way Dietl, T. and Tschesche, H. (Hoppe Seylers Z Physiol Chem: 357(5): 657–665 (1976)) proved arginine residue is present in the active site of proteinases.

As yet another example, borates (at low concentrations) are known to inhibit glyceraldehyde-3-phophate dehydrogenase from human, pig and rabbit muscle. However, in greater concentration (above 6 mM) borates inhibit esterase and acetylphosphatase activities. (Wolny M: Eur J Biochem 80 (2): 551–556 (1977)).

An interesting biological activity of borates was noticed in the case of palytoxin induction of the histamine release from rat mast cells. In the presence of borates the activity of palytoxin was increased ten times (Chatwal G S, Ahnert-Hilger G, Beress I, Habermann E: Int Arch Allergy Appl Immunol 68 (2): 97–100 (1982)).

Borates inhibit methylation of catechol estrogen and pyrocatechol by catechol-O-methyltransferase (Beattie J H, Weersink E: J Inorg Biochem 46 (3): 153–160 (1992)).

Several naturally occurring antibiotics contain boron as an essential structural element, such as boromycin, an anti-HIV antibiotic (Kohno J, et al: Biosci Biotechnol Biochem (Japan) 60 (6), 1036–7 1996)), or tetralons, new boron-containing antibiotics from a Myxobacterium, Sporangium cellulosum (Irschik H, Schummer D, Gerth K, Hofle G, Reichenbach H: J Antibiot (Tokyo) (Japan) 48 (1): 26–30 (1995)).

Borates are experimentally used in surgery as agents which promote healing of open wounds (Humzah M D, Marshall J, Breach N M: J R Coll Surg Edinb (England) 41(4): 269–70 1996); McCowan M, Aikten F: J Wound Care (England) 6(5): 248–249 (1997); Bliss M R: J Wound Care (England) 6(5): 248–249 (1997)).

Larvicidal effects of ingestion of boric acid and disodium octaborate tetrahydrate by cat fleas was recently described by Hinkle N C., Koehler P G, and Patterson R S in J Med Entomol (United States) 32(4): 424–7 (1995).

Some specific organoboron compounds (such as cyanotriphenylborate) were shown to be subtype-specific blockers of glycine receptor chloride channels (Rundstrom N, Schmidien V, Betz H, Bormann J, Langosch D: Proc Acad Sci U S A (United States) 91(19): 8950–4 (1994)).

Treatment of chick embryo pelvic cartilage with 1–3% aqueous boric acid induces release of proteoglycans, collagen and TNF-alpha into the culture medium, but at the same time strongly decreases their intracellular synthesis. However, the same concentration of boric acid, in the presence of great molar excess of glucose in culture medium, does not decrease intracellular protein synthesis, but still stimulates protein secretion into the culture medium (Benderdour M, Hess K, Dzondo-Gadet M, Dousset B: Biochem Biophys Res Commun 234 (1): 263–8 (1997).

It has been proposed that borons interact actively with Ca-metabolism, but exact mechanisms of this interaction have not yet been determined (Nielsen F, Muller L, Gallagher S: J Tace Elem Exp Med 3: 45–54 (1990). Specific biological Ca—B interaction was also described by T. Maruyama et al (J Biochem (Tokyo) 122(3): 498–505 (1997)), who showed that 2-amonoethoxydiphenyl borate (2-APB) inhibited Ins (1,4,5)P3-induced Ca release from rat cerebral microsomal preparations. Addition of 2-APB to the extracellular environment inhibited the cytosolic Ca rise in intact cells such as human platelets and neutrophiles stimulated by thrombin or leukotriene B4 LTB4).

SUMMARY OF THE INVENTION

The present invention provides methods and compositions in which boron compounds/complexes having a central tetrahedral boron atom that is covalently bound to four ligands (of either identical or different nature), other than boric acid and boric acid salts, are utilized for rejuvenating of human skin.

In one aspect of preferred embodiments, the invention, the contemplated skin rejuvenating effects are any of the following: decreasing of skin wrinkles, improving of skin thickness, increasing of skin hydration, softness and elasticity, as well as improving the skin color and decreasing the number and size of age spots. Also specifically included among the preferred skin rejuvenating effects is increasing collagen production, which may be caused by increased incorporation of proline by the skin. The term "skin rejuvenating" is thus employed herein in its broadest possible manner, not only to indicate repair of damaged skin, but also to mean any improvement to the look and feel of the skin.

In another aspect of preferred embodiments, at least one of the ligands is contemplated to include an oxygen, nitrogen, carbon or sulfur atom, and in more preferred embodiments all four ligands are contemplated to include an oxygen, nitrogen carbon or sulfur atom. In especially preferred embodiments boron is complexed with a saccharide or an amino acid having at least two hydroxyl groups, or one amino- and one hydroxyl group in 1,2- or 1,3-position to each other. Such a spatial arrangement allows formation of stable five- or six-membered rings consisting of one boron atom, two heteroatoms and two or three carbon atoms. Such complexes may advantageously comprise fructose, sorbose, mannitol, sorbitol, xylitol, ascorbic acid, serine or threonine. In its complexes, boron is bound more or less tightly to heteroatoms.

Quantitatively speaking, the stability of boron complexes is contemplated to be proportional to their association constants, and In another aspect of preferred embodiments, preferred complexes have association constants of at least 50, and more preferred complexes have an association constant between 3,000 and 20,000.

In yet another aspect of preferred embodiments, acidic boron complexes may be further converted to salts having sodium, potassium, magnesium or calcium as a counter ion (cation). However, one can successfully used other non-toxic and non-irritating cations such as ammonium, alkyl-, dialkyl- and trialkyl-ammomium, or quaternary ammonium cations.

In another aspect of preferred embodiments, an active boron compound/complex is included in a suitable cosmetic formulation wherein the compound/complex is provided in a suitable solvent system, a microemuslion or macroemulsion form, or a suitable liposome form. These formulations may advantageously contain other ingredients that are also non-toxic and non-irritating to the skin. The compositions are also preferably adapted for efficient penetration through the skin stratum corneum barrier when applied topically.

Various objects, features, aspects and advantages of the present invention will become more apparent from the following description of preferred embodiments of the invention, along with the accompanying drawing.

DETAILED DESCRIPTION

We have discovered that boron compounds and complexes, other than boric acid and boric acid salts, are useful as skin rejuvenating agents. As used herein, the term skin rejuvenating agent means any biologically active substance that noticeably produces any of the following effects: decreasing skin wrinkles, improving skin thickness, increasing skin hydration, softness or elasticity, or decreasing the number or size of skin discolorations such as age spots.

Preferred Structures

Figure 1:
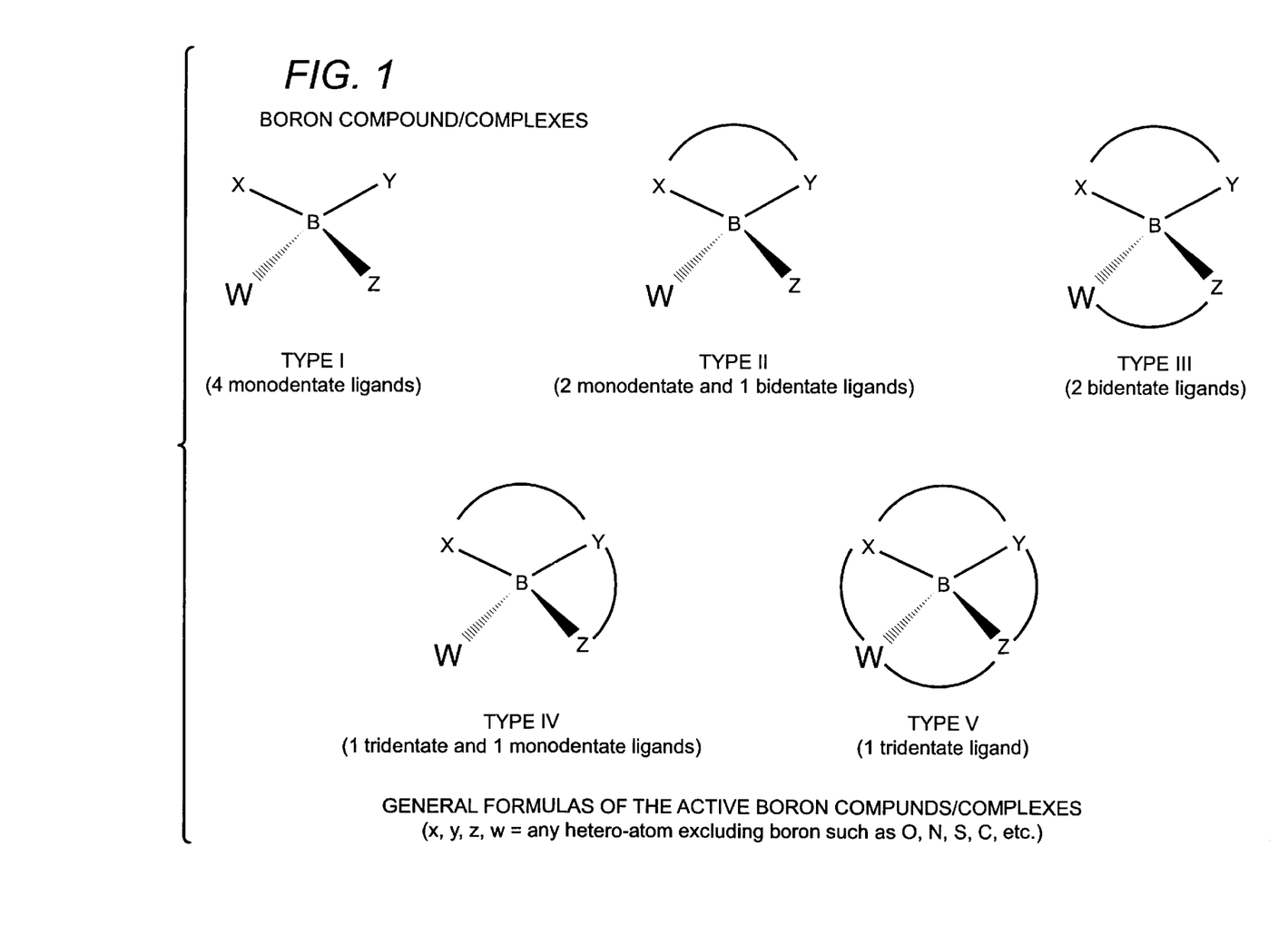
FIG. 1 depicts generic chemical structures of boron compounds/complexes according to the present invention.

FIG. 1 depicts a general structure of boron compounds suitable for skin-rejuvenating purpose. As discussed elsewhere herein, residues W, X, Y and Z may be the same as, or different from one another, and are contemplated to include any suitable heteroatom. As used herein, the term heteroatom means any chemical element except boron. Preferably, hetero-atoms include oxygen, nitrogen, carbon and sulfur, but are also contemplated to include hydrogen and non-metallic elements from groups IVA, VA, VIA and VIIA of the periodic table of elements.

Although the ligands may range from the very simple to the very complex, preferred ligands have moderate complexity, and include especially sugars, sugar polyols, amino acids and other non-toxic boron specific ligands. Where rings are involved, five-membered rings are preferred over six-membered rings, and six-membered rings are preferred over hepta-membered rings, and so forth.

It is further contemplated Boron compounds/complexes can be natural, synthetic, or some combination of natural and synthetic. Thus, it is contemplated to use boron complexes that exist in nature such as glyco-borates and sugar polyolo-borates, both of which are often found in fruits. For practical reasons, these naturally occurring boron compounds are best synthesized, although they could be extracted from natural sources.

It is particularly contemplated that boron compounds may be complexed with metal or other ions that charge neutralize the boron anionic complex. Preferred such complexing agents include any of a variety of non-toxic metallic cations, such as sodium, potassium, calcium, or magnesium. One can, however, also successfully use ammonium cation, monoalkyl-, dialkyl- or trialkyl-ammonium cations, as well as quaternary ammonium cations. Still further, one can use acidic form of the boron complex in which the counter cation is hydronium ion (proton) or the corresponding undissociated acidic form of the complex. As used herein, the various forms of the term "boron compound/complex" are used generically in the broadest possible sense to mean boron compounds that are not complexed and/or boron compounds that are complexed.

Generally speaking, we contemplate that the higher the association constant of the boron complex, the less toxic is the complex, and the more advantageous are its biological properties. In a quantitative sense, association constants at or above about 50 are usable, although ones of over 1,000 are preferable. In the most favorable cases, association constants between about 3,000 and about 20,000 are especially beneficial.

Figure 2A:
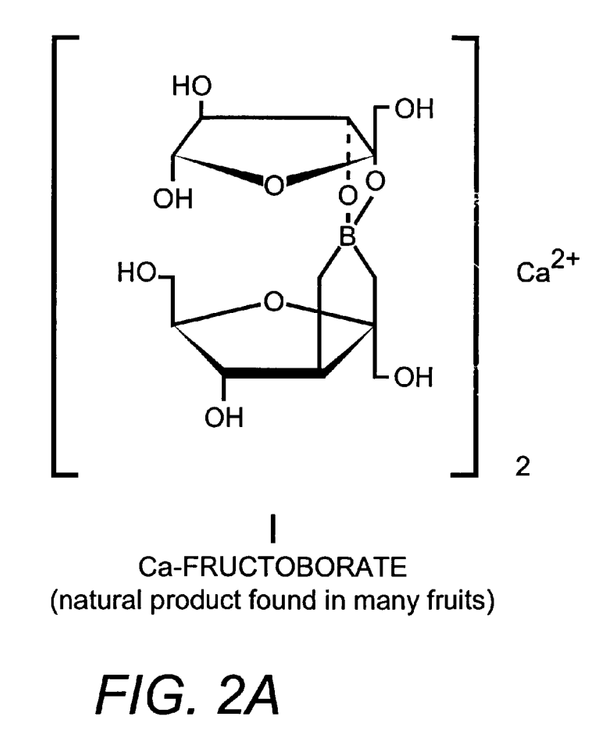
FIGS. 2A and 2B are chemical structures depicting particularly preferred isomers of calcium fructo-borate complex and calcium threonino-borate complex.
Figure 2B:
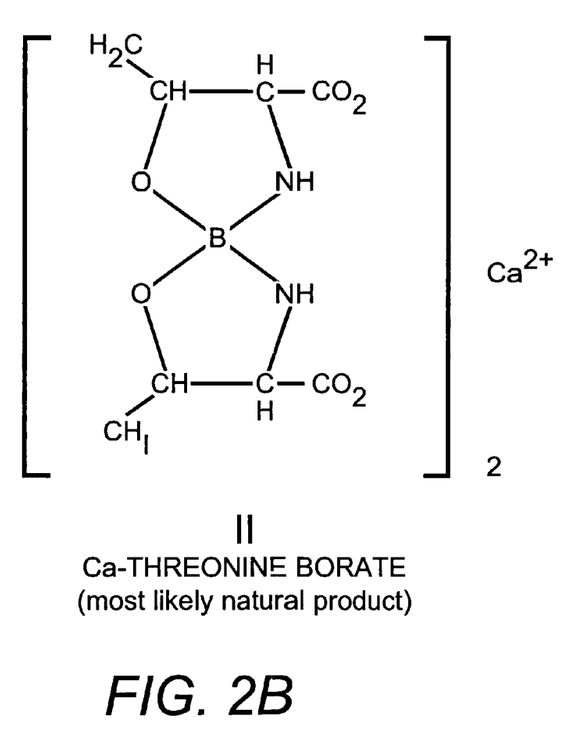

FIG. 2A depicts a particularly preferred complex, calcium fructo-borate, illustrated in one of several possible structural isomeric forms (which are interconvertible among themselves thus making a thermodynamically defined equilibrium). FIG. 2B depicts another particularly preferred isomeric form of calcium threonino-borate.

Applications

In one aspect of preferred embodiments, Boron compounds/complexes contemplated herein may be taken orally as nutritional supplements. Also, such compounds/complexes may be placed in solution, emulsion, microemulsion, cream or ointment and applied topically to the skin.

When applied as a topical compound, i.e., onto the surface of intact skin, the boron compounds/complexes may advantageously be included in a solution or emulsion in any lipid, non-lipid, or mixed lipid and non-lipid carrier(s) suitable for topical application. It is especially contemplated that the carrier may include water, aqueous buffer, a mixture of water and an organic solvent allowed in topical skin treatment (such as ethanol, glycerol, etc), organic non-toxic and non-irritating solvents, or macro- and micro-emulsion forms, liposome forms.

Particularly preferred carriers are liposome and microemulsion formulations, and at present the most preferred carriers are (micro) emulsions based on neutral triglyceride oils, and emulators such as soybean lecithin, bile acid salts, polyethyleneglycolized triglycerides and various polyethylene glycol derivatives. Such formulations are contemplated to efficiently penetrate the skin stratum corneum barrier, and dermis. As used herein, the term "solution" is used a broad lay sense to mean any substance dispersed in a carrier. Thus, according to the definition used herein, boron compound/complex solutions include mixtures of boron containing compounds and /or complexes in all manners of solvents, whether homogeneously or non-homogeneously dispersed, completely or partially solvated, suspended, emulsified, or dispersed in any other manner. Boron compound/complex solutions thus also include all possible carriers.

Especially preferred concentrations of solutions/emulsions have about $10^{-6}$ to 10 weight % of boron, with solutions/emulsions containing 1–5 mg of B per ml contemplated to be particularly suitable for skin-rejuvenating purposes. Such solutions/emulsions are contemplated to be rubbed onto the skin several times per day, especially morning and evening, preferably after a shower or bath. Concentrations of the boron compounds/complexes not specifically mentioned may also advantageously contain $10^{-6}$ to 10 weight % of boron.

A particularly preferred method of application comprises soaking the skin of a user in a boron salt complex as contemplated herein. The soaking preferably takes place in a bath of water containing the salt, in which the user is partially or fully immersed. The soaking can thus take place using a boron bath salt in a manner analogous to that now known for Epsom Salts (magnesium sulfate). In such instances, the bath salt may contain anywhere from 20 weight % to 100 weight % of the boron salt complex.

In other embodiments, the salt can be dissolved in water, and then applied using a cloth, sponge, or other absorbent material. In any case, immersion or other soaking application may then advantageously be followed by topical application of a cream to hands and/or face, or any other part of the skin where a rejuvenating effect is needed.

In addition to soaking aids and creams, it contemplated that the boron compounds/complexes contemplated herein can be applied topically in any other suitable manner. Thus, it is contemplated to include boron compounds/complexes in lipsticks and other cosmetics, shampoos, deodorants and so forth. To conveniently refer to all such forms, we employ the term generic term, topical skin care products.

Without being limited to the validity or applicability of any particular mechanism or mode of action, it is contemplated here that the boron compounds/complexes contemplated herein stimulate skin rejuvenation through interaction with a broad range of enzymes and enzymes systems, or gene-controlling systems, as opposed to targeting a single enzyme or enzyme system. Such systems are present to a greater or lesser extent across a broad range of animals, and it is thus contemplated that the inventive subject matter is broadly applicable to humans, other mammals, as well as other animals.

Figure 3:
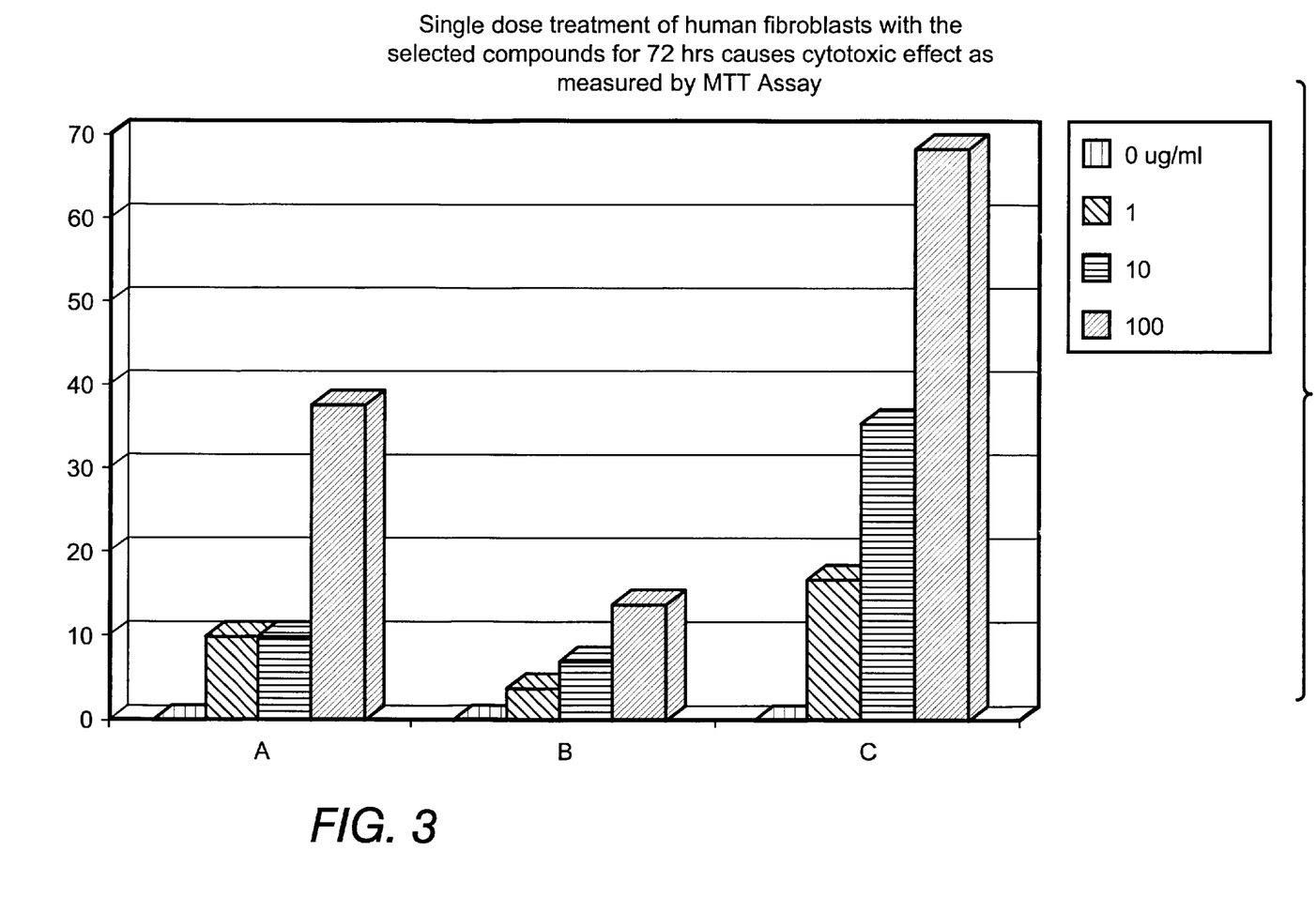
FIG. 3 is a graph of experimental results that demonstrate minimal cytotoxic effects (on normal human fibroblasts) of sodium borate (A), sodium fructo-borate (B) and sodium salicylato-borate (C) at different concentration levels measured by MTT assay.

In addition, without being limited to particular objects and advantages, it is contemplated that there are numerous potential advantages of the methods and compositions discussed herein. Among other things, selected boron compounds/complexes from this invention, and in particular ones containing natural sugars, sugar polyols, and amino acids, are considerably less toxic than boric acid and its simplest derivatives as it was shown in the case of sodium fructoborate (FIG. 3). Such boron compounds/complexes are thus safer than boric acid itself or its simple derivatives for prolonged topical applications, including long term treatments for skin-rejuvenating purposes. Another advantage is that many of the boron compounds/complexes contemplated herein are stable at room temperatures, storable in their suitable formulations for a long time and are commercially readily available. Still another advantage is that many of the boron compounds/complexes contemplated herein are expected to show multifunctional synergistic biological activity. This represents a great advantage to other previously described skin-rejuvenating agents, all of which were specifically active towards one particular enzyme.

Synthesis

Boron compounds/complexes employed according to the present invention can be prepared in any suitable manner. In an exemplary synthesis, sodium borate/tetraborate is treated with two molar equivalents of sugar polyol (preferably mannitol or xylitol), or two molar equivalents of an amino acid (preferably serine or threonine), in an aqueous solution. Generally, isolation of the formed complex is not necessary since the aqueous solution is immediately used for the preparation of the final formulation of the product (such as in an emulsion, microemulsion or liposome form). However, if necessary, the isolation of the boron compound/complex is readily achievable. In these cases, usually, an excess of ethanol (or acetone) is added to aqueous solution of a boron compound/complex, whereupon the boron complex crystallizes out. The solid product can be recrystallized if needed using corresponding standard laboratory or industrial techniques and non-toxic solvents.

It is also contemplated that other ligands (mono-, di- and/or poly-valent), in the corresponding molar ratio to the starting boron compound, can be simply mixed in an appropriate solvent (water, acetone, dioxan, tetrahydrofuran, etc), whereupon the complex directly crystallizes out, or stays in a solution.

Experimental Results

FIGS. 3–7 illustrate results of experiments designed to elucidate some of the biological properties that may be present in contemplated boron compounds/complexes. In these examples, we studied the action of two boron complexes: sodium fructo-borate (SFB) and sodium salicylato-borate (SSB), upon normal human fibroblasts, in comparison to untreated fibroblasts and ones treated with boric acid (BA, uncomplexed with any ligand). FIG. 3 depicts results of a single dose treatment of human fibroblasts with increasing concentrations of BA, SFB and SSB for 72 hours in order to determine their cytotoxic effects (by MTT assay). According to these results, the least toxic compound is SFB, which is almost 4 times less toxic than BA itself, at their tested concentration level of 100 ug/ml.

Figure 4:
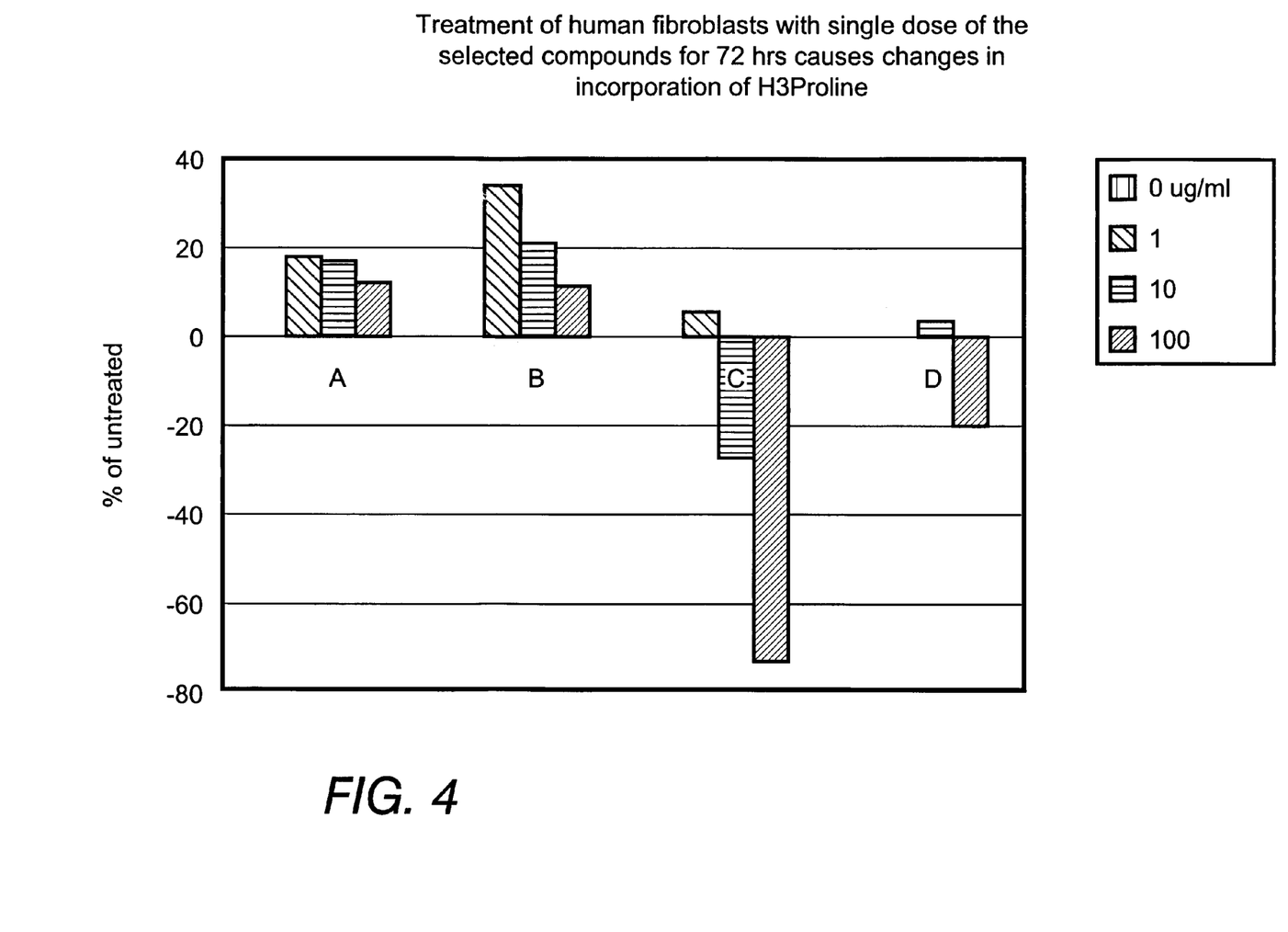
FIG. 4 is a graph depicting experimental results of H3Proline incorporation (in human fibroblasts) upon treatment with A, B, and C compared to untreated cells.

FIG. 4 depicts results from treatment of normal human fibroblasts with a single dose of BA, SFB and SSB for 72 hours, whereupon the final degree of incorporation of H3Proline was determined. The degree of H3Proline incorporation is a measure of the ongoing biosynthesis of collagen in treated cells. Again, the most beneficial effect was determined for SFB.

Figure 5:
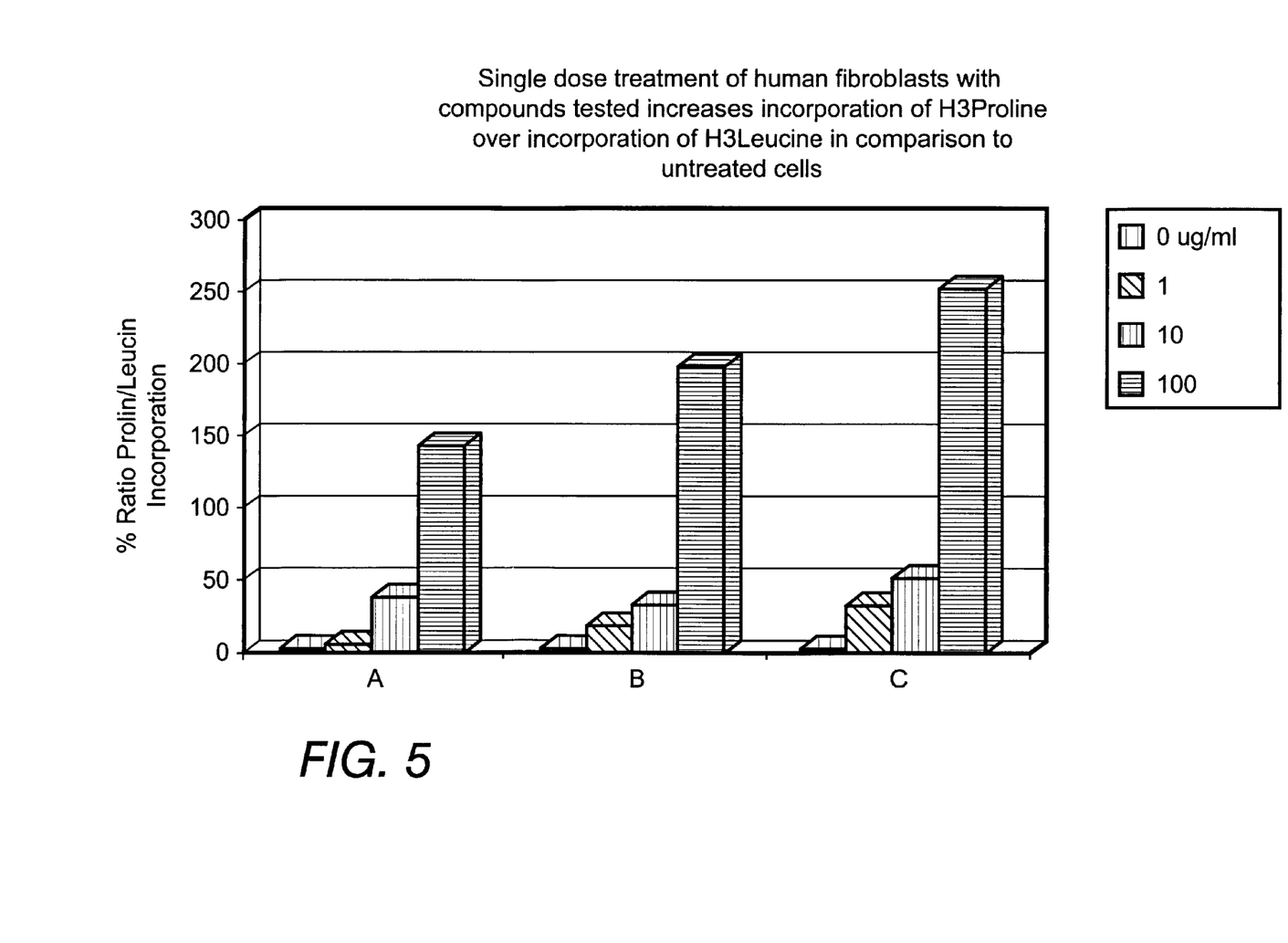
FIG. 5 is a graph depicting experimental results of H3Proline/H3Leucine incorporation in human fibroblasts upon treatment with A, B, and C, compared to untreated cells.

FIG. 5 depicts the results of a single dose treatment of human fibroblasts with BA, SFB and SSB regarding the preferred incorporation of H3Proline over H3Leucine in comparison to untreated cells. In this experiment, SSB showed the best performance, while SFB was quite close to it. Since SSB shows rather pronounced cytotoxicity, use of SFB would be overall much more biologically beneficial.

Figure 6:
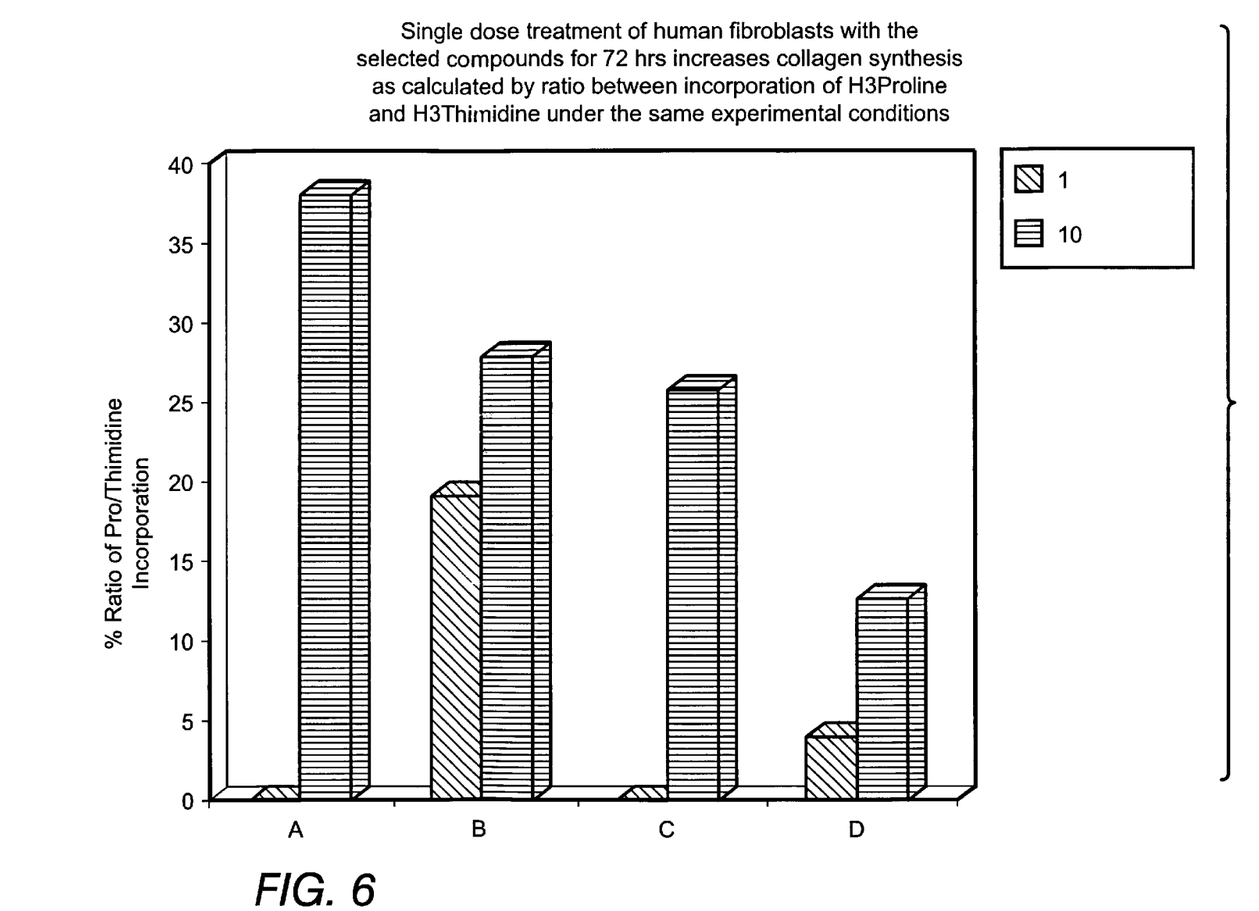
FIG. 6 is a graph depicting experimental results of increase of collagen synthesis (measured by determination of ratio between incorporation of H3Proline and H3Thymidine) in human fibroblasts by treating them with A, B and C, compared to untreated cells.

FIG. 6 depicts the results of a single dose treatment of normal human fibroblasts with the selected compounds for 72 hours, in which case the increase of collagen synthesis was calculated by ratio between incorporation of H3Proline over the incorporation of H3Thymidine under the same experimental conditions. In this experiment, SFB was best at the concentration of 1 ug/ml, while at the concentration of 10 ug/ml its activity was next to BA. Overall, due to its least toxicity, SFB showed the most beneficial biological properties. These properties are of special value for skin-rejuvenation purposes.

Figure 7:
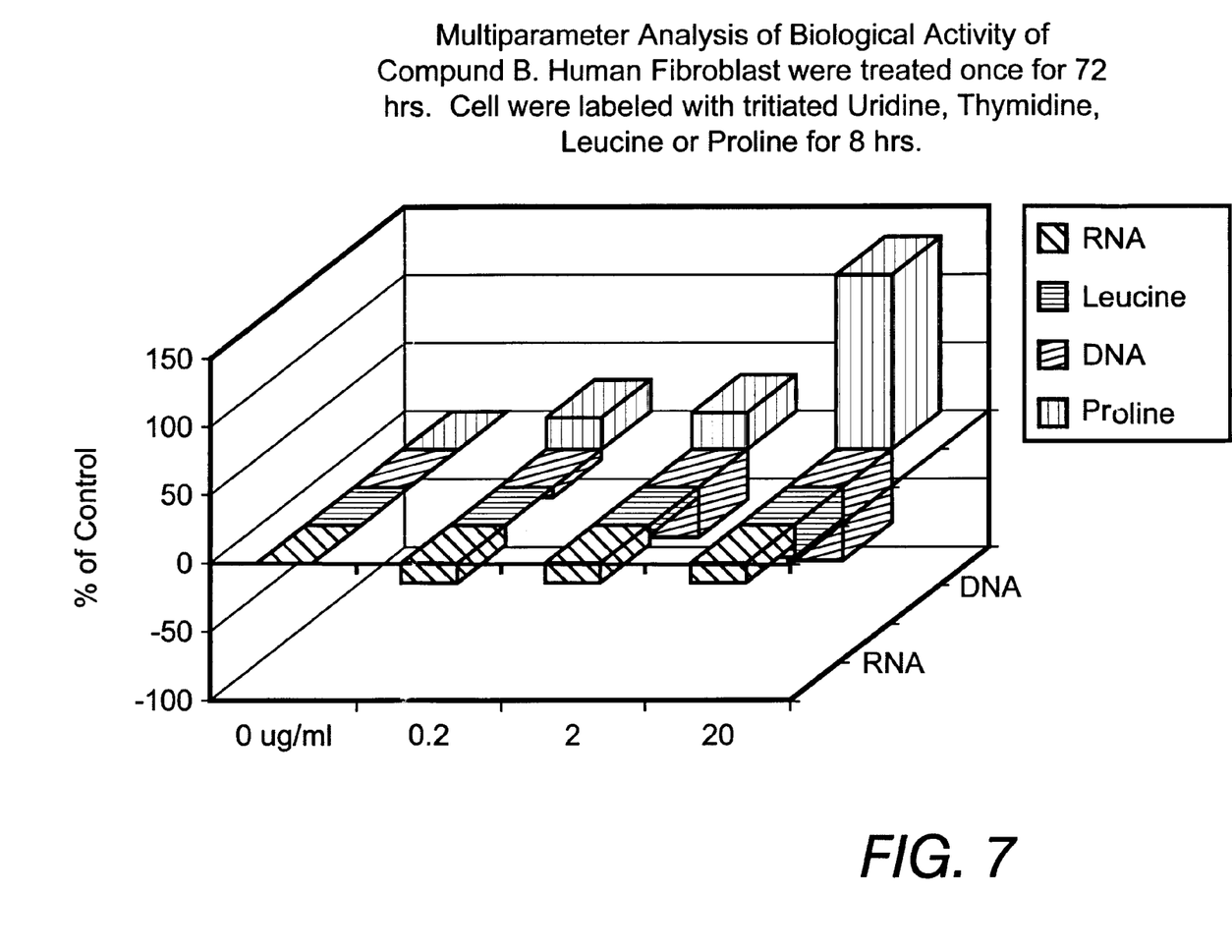
FIG. 7 is a graph depicting a multi-parameter analysis of biological activity of complex B.

FIG. 7 depicts a multi-parameter analysis of biological activity of SFB. The overall effects (determined by labeling cells with tritiated Uridine, Thymidine, Leucine and Proline for 8 hours) are quite favorable and beneficial, especially if one has in mind skin-rejuvenating processes.

EXAMPLES

General Remarks

When synthesizing boron compounds/complexes according to the present disclosure, one should generally follow accepted rules of chemical synthesis. Thus, if a ligand contains only one hetero-atom in its B-binding site, one takes at least four molar equivalents (often an excess from practical reasons) of that ligand in respect to one molar equivalent of the starting boron compound. Further, if a ligand contains two or three hetero-atoms in its B-binding sites, one takes two or more molar equivalents of it in respect to one molar equivalent of the starting boron compound. Still further, if a ligand contains four or more hetero-atoms in its B-binding sites, one takes one or more molar equivalents of the ligand to one molar equivalent of the starting boron compound. At this point, one should take into account some empirical rules. Namely, many naturally occurring saccharides contain a large number of hydroxyl groups. However, not all of them are capable of binding boron atom. For example, mannitol contains 6 hydroxyl groups, but uses only two of them for B-binding. Consequently, mannitol is to be considered as a two-dentate ligand. In other words, one has to know the chemical properties of a ligand to calculate an exact number of its B-binding sites and thus to come up with its correct molar equivalent.

Of course, the molar equivalent of the starting boron compound corresponds to its molecular formula if it contains one boron atom in it. If molecular formula contains more than one boron atom one divides molecular formula with a number of boron atoms containing in it. For example, if one starts with sodium tetraborate decahydrate, its molecular formula (molecular weight) should be divided by four to obtain its molar equivalent.

General Preparation Procedure of Boron Compounds/Complexes

As a rule, the selected ligand, in the corresponding or slightly higher molar ratio to the starting boron compound and the starting boron compound (most often boric acid or borax), is mixed in water to make a rather concentrated solution (usually in the range from 10 to 30%). The reaction mixture is stirred or shaken at room temperature for 0.5 to 1 hour, whereupon all solid components, as a rule, go completely to a solution. If boric acid is used, then usually subsequent neutralization is needed, such as with sodium bicarbonate, potassium bicarbonate, or calcium carbonate (the latter, if used in needed molar equivalent ratio to starting boron compound, goes completely at the end of reaction to a solution; since calcium carbonate is water insoluble reactant, its final water solubilization represents a useful practical parameter to for evaluation of the reaction completion)

Reaching this point, one can proceed further according to one of two general possibilities: (1) using the prepared solution (in undiluted or diluted form) for the final formulation preparation, or if one needs pure and chemically better defined complexes; and (2) using the prepared solutions for the isolation and purification of the desired B-complex.

In carrying out detailed experimental work, one uses standard procedures and techniques that are familiar to a person trained in the field of inorganic/organic synthetic preparations. However, for illustrative purposes bellow given examples should clarify certain important experimental details.

Example 1—Calcium Mannitolo-borate

Boric acid (1.24 g; 20 mmoles) and mannitol (7.28 g; 40 mmoles) are dissolved in water (20 ml) at 60°–70° C. After cooling down to room temperature, solid calcium carbonate (1 g; 10 mmoles) is gradually added to the solution. During the addition of calcium carbonate carbon dioxide is evolved. When all calcium carbonate is dissolved and carbon dioxide evolution ceased (which lasts about 30 minutes), one adds ethanol (80 ml). Viscous (semi-solid) heavy layer separates out and the upper aqueous-ethanol solution is decanted off. A new portion of ethanol is added (80 ml), whereupon, on stirring at room temperature for a while, the crystalline complex separated out.

The same is filtered off and washed with ethanol (40 ml). After drying the complex in vacuum desiccator, one obtains pure crystalline Ca-mannitolo-borate (7 g; 90% of theoretical yield). A similar procedure can be carried out using other cations, such as those of magnesium, sodium and potassium, and such may be preferred in topical skin treatment.

Example 2—Sodium Serino-borate (in aqueous solution)

Sodium tetraborate (0.804 g; 4 mmoles) and serine (3.2 g; 32 mmoles) are mixed in water (15 ml) at room temperature. After stirring or shaking for 0.5 to 1 hour at room temperature, all components go into solution. The final concentration is adjusted to the desired level (usually 2–4 mg B/ml).

Example 3—Liposome Formulation of Calcium Fructo-borate

Calcium fructo-borate (1 g) is dissolved in distilled water (50 ml). Separately, phosphatidyl choline (PC, 0.250 g in 25 ml of chloroform) is evaporated at room temperature in vacuum with a rotary evaporator to provide a uniform transparent lipid film.

The previously prepared water solution of calcium fructo-borate is added at once to a lipid PC-film. After shaking the mixture for 2 hours at 37° C., and sonicating the mixture for an additional 0.5 hour at room temperature, preparation of the calcium fructo-borate liposome formulation is finished.

Example 4—Ointment Formulation of Sodium Fructo-borate

Commercially available polyethyleneglycolized medium chain triglycerides (such as "Labrasol", "Gatte Fosse Inc")

(10 g), polyethyleneglycolized triglycerides (such as "Gelucir 44", "Gatte Fosse Inc" (10 g), soybean lecithin granules (available from many companies) (5 g) and almond oil (20 g) are well homogenized in a mixer at 40–60 rpm (component A).

Separately, one prepares component B as a solution of boric acid (0.61 g; 10 mmoles), $NaHCO_3$ (0.840 g; 10 mmoles) and D-fructose (3.20 g; 20 mmoles) in distilled water (30 ml) Component B is then slowly mixed in the component A with a mixer at 40–60 rpm. One obtains an ointment formulation suitable for application to human skin.

Example 5—Cream Formulation of Sodium Ascorbato-borate

Glycerol mono-oleate (readily commercially available) (5 g), polyglycerol oleate ("Plurol Oleic", "Gatte Fosse Inc") (5 g), soybean lecithin granules (0.5 g), sodium cholate (0.3 g), tocoferol (0.5 g), gelucir 44 (2 g) and almond oil (10 g) are fully homogenized in a mixer at 40-rpm (component A).

Separately, ascorbic acid (0.5 g), sodium bicarbonate (0.25 g) and boric acid (0.1 g) are stirred in water (20 ml) for 0.5 hour at room temperature providing a clear solution (component B).

Component B is added gradually to component A while slowly mixing in a mixer at 40 rpm during 1 hour at room temperature. The product is a cream formulation containing 2,77 mg B per gram.

Thus, specific embodiments and applications of boron compounds/complexes have been disclosed. It should be apparent, however, to those skilled in the art that many more modifications besides those already described are possible without departing from the inventive concepts herein. The inventive subject matter, therefore, is not to be restricted except in the spirit of the appended claims.

What is claimed is:

1. A method of treating skin in an individual, comprising:

selecting a formulation demonstrated to provide skin rejuvenation when applied topically, said formulation including a boron containing structure having a central tetrahedral boron atom bound to four ligand sites, other than boric acid and boric acid salts, in an amount effective to produce a noticeable improvement in the skin; and applying the formulation to an area of skin.

2. The method of claim 1 wherein at least one of the ligands includes an atom selected from the group consisting of oxygen, nitrogen, carbon and sulfur that is directly attached to the boron atom.

3. The method of claim 1 wherein the boron atom is bound to a ligand to form a stable five- or six-membered ring comprising the boron atom, two hetero-atoms, and 2 or 3 carbon atoms.

4. The method of claim 3 wherein the ligand comprises a saccharide.

5. The method of claim 3 wherein the ligand comprises amino acid.

6. The method of claim 3 wherein the ligand is selected from the group consisting of fructose, sorbose, mannitol, sorbitol, xylitol, ascorbic acid, serine and threonine.

7. The method of claim 3 wherein the ligand has a structural element having at least two hydroxyl groups in a 1,2- and a 1,3-position relative to each other.

8. The method of claim 3 wherein the ligand has a structural element having at least one amino- and one hydroxyl group in a 1,2- and 1,3-position relative to each other.

9. The methods of any of claims 1–8 wherein the boron containing structure has an association constant of at least 3,000.

10. The methods of any of claims 1–8 wherein the boron containing structure is in the form of a salt.

11. The methods of claim 10 wherein the salt includes a cation selected from the group consisting of sodium, potassium, magnesium, calcium, zinc and copper.

12. The methods of any of claims 1–8 wherein the formulation comprises at least one of an emulsion, a microemulsion, a nanoemulsion, and a liposome.

* * * * *